United States Patent
Bowen et al.

(10) Patent No.: US 8,263,356 B2
(45) Date of Patent: Sep. 11, 2012

(54) ANTIBODIES AND METHODS FOR PREDICTING DENTAL CARIES

(75) Inventors: William H. Bowen, Victor, NY (US); Anne Vacca Smith, Rochester, NY (US); Robert Berkowitz, Pittsford, NY (US)

(73) Assignee: University of Rochester, Rochester, NY (US)

( * ) Notice: Subject to any disclaimer, the term of this patent is extended or adjusted under 35 U.S.C. 154(b) by 729 days.

(21) Appl. No.: 11/464,378

(22) Filed: Aug. 14, 2006

(65) Prior Publication Data
US 2007/0065886 A1   Mar. 22, 2007

Related U.S. Application Data

(60) Provisional application No. 60/707,701, filed on Aug. 12, 2005.

(51) Int. Cl.
G01N 33/53      (2006.01)
G01N 33/536     (2006.01)
G01N 33/543     (2006.01)
G01N 33/569     (2006.01)
G01N 33/573     (2006.01)
G01N 33/577     (2006.01)
C07K 16/12      (2006.01)
C07K 16/40      (2006.01)
C12P 21/08      (2006.01)

(52) U.S. Cl. ...... 435/7.4; 435/7.34; 435/7.92; 435/7.95; 435/15; 435/885; 436/512; 436/518; 436/536; 436/164; 436/172; 530/388.26; 530/389.1; 530/866

(58) Field of Classification Search ............ 435/7.34, 435/7.4, 7.92, 15, 287.2, 885, 975, 7.95; 436/512, 518, 536, 164, 172; 530/388.26, 530/389.1, 866
See application file for complete search history.

(56) References Cited

U.S. PATENT DOCUMENTS

| 4,150,116 A * | 4/1979 | Taubman et al. .......... 424/244.1 |
| 4,888,170 A * | 12/1989 | Curtiss, III ................. 424/200.1 |
| 2003/0113823 A1 | 6/2003 | Gregory et al. |
| 2003/0124635 A1 | 7/2003 | Ukaji et al. |

FOREIGN PATENT DOCUMENTS

| JP | 2002-267673 | * | 9/2002 |
| WO | 2006019118 A1 | | 2/2006 |

OTHER PUBLICATIONS

Nanbu et al., 2000. Production, characterization, and application of monoclonal antibodies which distinguish four glucosyltransferases from *Streptococcus sobrinus*. FEMS Immunology and Medical Microbiology 27: 9-15.*
Rudikoff et al., 1982. Single amino acid substitution altering antigen-binding specificity. Proc Natl Acad Sci USA 79: 1979-1983.*
Mattos-Graner et al., 2000. Water-insoluble glucan synthesis by mutans streptococcal strains correlates with caries incidence in 12- to 30-month-old children. J. Dent. Res. 79: 1371-1377.*
Fukushima et al., "Production, Characterization, and Application of Monoclonal Antibodies Which Distinguish Three Glucosyltransferses from *Streptococcus* Mutans," Infection and Immunity 61(1):323-8 (1993).
Supplementary Partial European Search Report for International Patent Application PCT/US2006031639 (Jul. 30, 2008).
Wunder et al., "Effects of Antibodies to Glucosyltransferase on Soluble and Insolubilized Enzymes," Oral Diseases 6 (5):289-96 (2000).

* cited by examiner

Primary Examiner — Gail R Gabel
Assistant Examiner — James L Grun
(74) Attorney, Agent, or Firm — LeClairRyan, a Professional Corporation

(57) ABSTRACT

The present invention relates to antibodies, binding portions thereof, or probes that bind specifically to glucosyltransferase enzymes, and uses of these agents for detecting glucosyltransferase enzyme(s) in a sample and for diagnosing predisposition of a human child to early childhood caries. The present invention also relates to a kit for detecting a glucosyltransferase enzyme in an oral sample from an animal.

7 Claims, 5 Drawing Sheets

ANTIBODIES AND METHODS FOR PREDICTING DENTAL CARIES

This application claims the priority benefit of U.S. Provisional Patent Application Ser. No. 60/707,701, filed Aug. 12, 2005, which is hereby incorporated by reference in its entirety.

The subject matter of this application was made with government support under National Institutes of Health Grant No. DE015564. The U.S. Government has certain rights in the invention.

FIELD OF THE INVENTION

The present invention relates to antibodies, binding portions thereof, or probes to glucosyltransferase enzyme and uses of these agents for detecting glucosyltransferase enzyme in a sample, for diagnosing dental caries in a patient, or diagnosing predisposition of a human child to early childhood caries.

BACKGROUND OF THE INVENTION

Early childhood caries (also referred to herein as "ECC"), which involves tooth decay of primary teeth in young children, is a major public health problem. See Centers for Disease Control and Prevention: Conference, Atlanta (September, 1994); Tinanoff et al., "Early Childhood Caries: Overview and Recent Findings," *Pediatric Dentistry* 19:12-16 (1997); Tinanoff, "Introduction to the Early Childhood Caries Conference: Initial Description and Current Understanding," *Commun Dent Oral Epidemiol* 23(Suppl. 1):5-7 (1998). A reliable test for caries activity before appearance of lesions does not exist.

Glucosyltransferases ("Gtfs") play an essential role in the etiology and pathogenesis of dental caries by promoting the sucrose dependent adherence of cariogenic streptococci on smooth surfaces and the subsequent development of dental plaque (Smith et al., "Effects of Local Immunization with Glucosyltransferase on Colonization of Hamsters by *Streptococcus mutans*," *Infect Immun* 37:656-661 (1982); Hamada et al., "Virulence Factors of *Streptococcus mutans* and Dental Caries Prevention," *J Dent Res* 63:407-411 (1984); Tanzer et al., "Virulence of Mutants Defective in Glucosyltransferase, Dextran-Meditated Aggregation, or Dextranase Activity, in *Molecular Basis of Oral Microbial Adhesion*, Mergenhagen et al., eds., Washington, D.C.: American Society for Microbiology, pp. 204-211 (1985); Tsumori et al., "The Role of the *Streptococcus mutans* Glucosyltransferases in the Sucrose-Dependent Attachment to Smooth Surfaces: Essential Role of the Gtf-C Enzyme," *Oral Microbiol Immunol* 12:274-280 (1997)).

The colonization of smooth surfaces by mutans streptococci has been correlated with high caries activities in young children and the synthesis of insoluble glucan has been shown to contribute to caries development in infant and toddlers by increasing the adherence of mutans streptococci and their accumulation in dental plaque (Alaluusua et al., "*Streptococcus mutans* Establishment and Dental Caries in Children from 2 to 4 Years Old," *Scan J Dent Res* 91:453-457 (1983); Köhler et al., "The Earlier the Colonization by Mutans Streptococci, the Higher the Caries Prevalence at 4 Years of Age," *Oral Micrbiol Immunol* 3:14-17 (1988); Mattos-Graner et al., "Water-Insoluble Glucan Synthesis by Mutans Streptococcal Strains Correlates with Caries Incidence in 12- to 30-Month-Old Children," *J Dent Res* 79:1371-1377 (2000)).

Gtf B, C, and D are produced by cariogenic streptococci such as *Streptococcus mutans* and *S. sobrinus* (Hamada et al., "Biology, Immunology, and Cariogenicity of *Streptococcus mutans*," *Microbiol Rev* 44:331-384 (1980); Loesche, "Role of *Streptococcus mutans* in Human Dental Decay," *Microbiol Rev* 50:353-380 (1986)). The mutans streptococci synthesize at least three gtfgene products (Loesche, "Role of *Streptococcus mutans* in Human Dental Decay," *Microbiol Rev* 50:353-380 (1986); Hanada et al., "Isolation and Characterization of the gtfC Gene, Coding for Synthesis of Both Soluble and Insoluble Glucans," *Infect Immun* 56:1999-2005 (1988)). GtfB polymerizes an insoluble glucan composed predominantly of $\alpha1,3$ linked glucose moieties. GtfD produces a soluble glucan, which has predominantly $\alpha1,6$ linked glucosyl units, and GtfC synthesizes a polymer with a mixture of $\alpha1,3$ linked glucose moieties and $\alpha1,6$ linked glucose (Loesche, "Role of *Streptococcus mutans* in Human Dental Decay," *Microbiol Rev* 50:353-380 (1986); Hanada, et al., "Isolation and Characterization of the *Streptococcus mutans* gtfD Gene, Coding for Synthesis of Primer Dependent Soluble Glucan Synthesis," *Infect Immun* 57:2079-2085 (1989)). Although Gtf enzymes are found in whole saliva and in salivary pellicle formed in vivo and in vitro, the source and type are undetermined. There could be numerous sources of Gtf in saliva, and salivary Gtf could be derived from *S. mutans*, *S. sobrinus*, and *S. sanguinus* (Hamada, et al., "Biology, Immunology, and Cariogenicity of *Streptococcus mutans*," *Microbiol Rev* 44:331-384 (1980); Loesche, "Role of *Streptococcus mutans* in Human Dental Decay," *Microbiol Rev* 50:353-380 (1986); Vacca Smith et al., "In situ Studies of Pellicle Formation on Hydroxyapatite Discs," *Archs Oral Biol* 45:277-291 (2000)). Evidence shows that the Gtf activity found in salivary pellicle has many properties similar to those of GtfC (Vacca Smith et al., "Characterization of Glucosyltransferase of Human Saliva Adsorbed onto Hydroxyapatite Surfaces," *Caries Res* 30:354-360 (1996)).

In a recent study, the concentration of mutans streptococci in the saliva of caries-free and caries-active toddlers was quantified, and the bacteria were isolated and analyzed for their ability to produce glucan and adhere to glass surfaces (Mattos-Graner et al., "Water-Insoluble Glucan Synthesis by Mutans Streptococcal Strains Correlates with Caries Incidence in 12- to 30-Month-Old Children," *J Dent Res* 79:1371-1377 (2000)). These investigators found positive correlations between mutans streptococci levels in saliva and caries incidence, between Gtf activities of the mutans streptococci and caries incidence, and between Gtf activities of the bacteria and the abilities of the bacteria to adhere to glass surfaces (Mattos-Graner et al., "Water-Insoluble Glucan Synthesis by Mutans Streptococcal Strains Correlates with Caries Incidence in 12- to 30-Month-Old Children," *J Dent Res* 79:1371-1377 (2000)).

Gtf B, C and D are essential for the expression of virulence of mutans streptococci (DeStoppelaar et al., "Decrease in Cariogenicity of a Mutant of *Streptococcus mutans*," *Archs Oral Biol* 16:971-975 (1971); Hamada et al., "Virulence Factors of *Streptococcus mutans* and Dental Caries Prevention," *J Dent Res* 63:407-411 (1984); Tanzer et al., "Virulence of Mutants Defective in Glucosyltransferase, Dextran-Meditated Aggregation, or Dextranase Activity, in *Molecular Basis of Oral Microbial Adhesion*, Mergenhagen et al., eds., Washington, D.C.: American Society for Microbiology, pp. 204-211 (1985); Yamashita et al., "Role of the *Streptococcus mutans* gtf Genes in Caries Induction on the Specific-Pathogen-Free Rat Model," *Infect Immun* 61:3811-3817 (1993)).

The best predictor of future caries experience thus far involves assessing the presence of carious lesions already present on tooth surfaces (Grainger et al., "Determination of Relative Caries Experience," *J Can Dent Ass* 26: 531 (1960); Stamm et al., "The University of North Carolina Caries Risk Assessment Study: Final Results and Some Alternative Modeling Approaches," in Cariology for the Nineties," Bowen et al., eds., Rochester, N.Y.: University of Rochester Press, pp. 209-234 (1993); Hausen, "Caries Prediction-State of the Art," *Community Dent Oral Epidemiol* 25:87-96 (1997); Powell, L. V., "Caries Prediction: A Review of the Literature," *Community Dent Oral Epidemiol* 26:361-371 (1998); Messer, L. B., "Assessing Caries Risk in Children," *Aust Dent J* 45:6-10 (2000)). That is, current diagnostic procedures are limited to confirming the existence of active dental caries after damage has already occurred.

Despite the knowledge of causative factors for caries development, there exists a significant need for a quick and convenient test that can accurately assess caries activity chairside in affected individuals and be used reliably to predict the chance of developing carious lesions prior to onset.

The present invention is directed to overcoming these and other deficiencies in the art.

SUMMARY OF THE INVENTION

A first aspect of the present invention relates to an antibody or binding fragment thereof that specifically binds to a glucosyltransferase enzyme. Preferred antibodies or binding fragments are monoclonal antibodies or monoclonal antibody binding fragments, or mono-specific polyclonal serum.

A second aspect of the present invention relates to an immunological kit for detecting a glucosyltransferase enzyme in an oral sample from an animal. The kit includes an antibody or binding fragment that specifically binds to a glucosyltransferase enzyme. The kit further includes a reaction platform for contacting the antibody or binding fragment to the oral sample. The kit can be used for, inter alia, diagnosing the animal's predisposition to dental caries, particularly though not exclusively in children.

A third aspect of the present invention relates to a method of detecting a glucosyltransferase enzyme in a sample. This method involves providing an antibody or binding portion thereof or probe that specifically binds to a glucosyltransferase enzyme. The antibody or binding portion thereof or probe is contacted with a sample under conditions effective to yield a detectable signal if the glucosyltransferase enzyme is present in the sample and if the antibody or binding portion thereof or probe binds to at least a portion of the glucosyltransferase enzyme. A determination is then made as to whether the sample yields the detectable signal, where the presence of the detectable signal indicates that the sample contains the glucosyltransferase enzyme.

A fourth aspect of the present invention relates to a method of diagnosing predisposition of a human child to early childhood caries. This method involves performing the method of the third aspect of the invention using an oral sample (e.g., saliva) from a human child, where the presence of the detectable signal indicates that the sample contains the glucosyltransferase enzyme and that the human child is predisposed to early childhood caries.

Early childhood caries constitutes a major public health problem, and affects those who are least able to bear either the financial burden or the health burden. Children in underserved areas visit a physician more readily than a dentist. The monoclonal or monospecific antibodies of the present invention, raised to bind immunospecifically to Gtf enzymes, allow for a simple diagnostic test that can be performed in a single step. It is rapid and can be performed chairside. This is advantageous over the current diagnostic procedures (identifying caries lesions after they develop), because it will allow a doctor to screen children for caries risk and refer those at risk to the dentist for institution of preventive procedures. The present invention is likely to play a key role in reducing the incidence of dental caries, and ultimately benefit both individuals that would otherwise develop dental caries as well as the public health system at large.

DETAILED DESCRIPTION OF THE INVENTION

Figure 1:
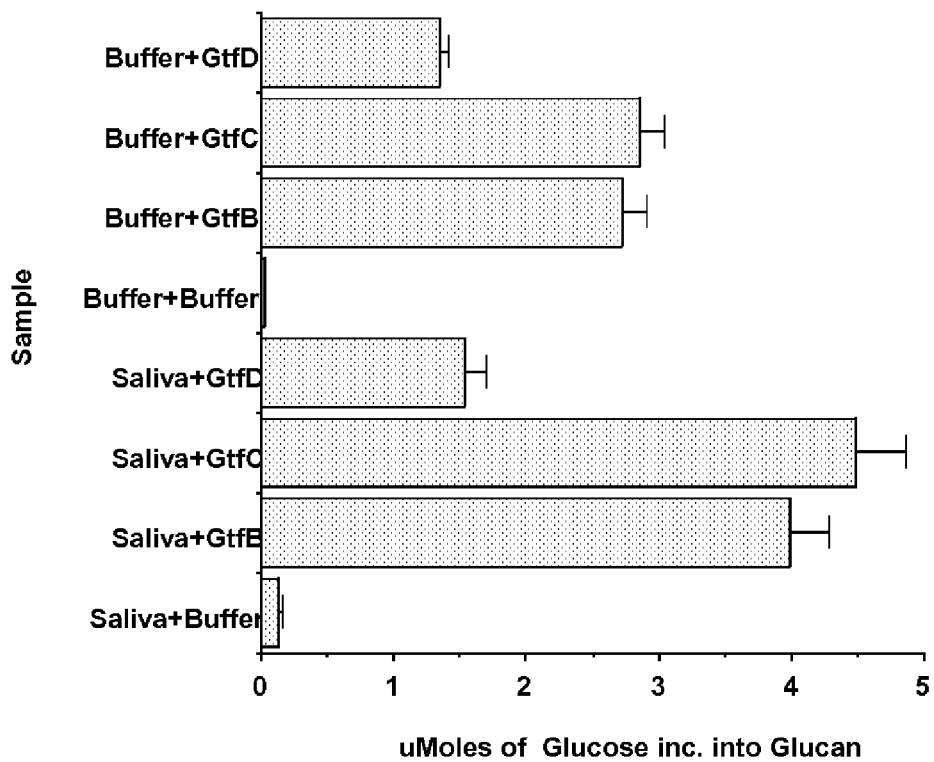
FIG. 1 is a bar graph showing the amount of glucan formation in samples containing Gtf, natural Gtf in whole human saliva, and combination of Gtf and saliva.

A first aspect of the present invention relates to an antibody or antibody fragment that specifically (i.e., immunospecifically) binds to a glucosyltransferase (Gtf) enzyme of cariogenic *Streptococci*. The Gtf is preferably Gtf B, C, or D from, e.g., *S. mutans* or *S. sobrinus*, or Gtf of *S. sanguinus* ("GtfSs").

The disclosed antibodies may be monoclonal or polyclonal, but preferably the antibodies are monoclonal or monospecific polyclonal.

Monoclonal antibody production may be effected by techniques which are well-known in the art. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature*, 256:495 (1975), which is hereby incorporated by reference in its entirety.

Mammalian lymphocytes are immunized by in vivo immunization of the animal (e.g., a mouse) with the protein or polypeptide of the present invention. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents (See Milstein and Kohler, *Eur. J. Immunol.*, 6:511

(1976), which is hereby incorporated by reference in its entirety). This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering the protein or polypeptide of the present invention subcutaneously to New Zealand white rabbits which have first been bled to obtain pre-immune serum. The antigens can be injected at a total volume of 100 µl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthanized (e.g., pentobarbital 150 mg/Kg IV). This and other procedures for raising polyclonal antibodies are disclosed in E. Harlow, et. al., editors, *Antibodies: A Laboratory Manual* (1988), which is hereby incorporated by reference in its entirety.

Polyclonal sera rendered monospecific for a particular target Gtf enzyme may be made, for example, by preparing a Gtf polyclonal antiserum using the procedures described above, and then exposing the polyclonal antiserum to hydroxyapatite beads coated with non-target Gtfs, thereby removing antibodies cross-reactive to non-target Gtf enzyme. Monospecificity for a particular Gtf enzyme can be determined by ELISA assay. For example, to determine whether the resulting monospecific antiserum can recognize endogenous Gtf in clarified whole human saliva, and exogenous target Gtf added to such saliva, clarified saliva from an animal (e.g., a human) can be mixed with either a buffer, GtfB, GtfC, GtfD or other Gtf, and the mixture coated onto an ELISA plate. The samples can then be probed with primary antisera, e.g., either anti-GtfB sera (for saliva alone or saliva mixed with GtfB), anti-GtfC sera (for saliva alone or saliva mixed with GtfC), or anti-GtfD sera (for saliva alone or saliva mixed with GtfD). Controls can consist of saliva/buffer or saliva/Gtf processed in the ELISA assay in the absence of primary antisera, and primary antisera exposed to plates coated with buffer alone. Absorbance analyses can then be performed to determine monospecificity for the target Gtf. Sera demonstrated to be monospecific can be employed in the assays of the present invention.

As indicated above, biological agents suitable for use in accordance with the present invention include antibodies, such as monoclonal or polyclonal antibodies. In addition, antibody fragments (antigen binding portions), half-antibodies, hybrid derivatives, probes, and other molecular constructs that are specific for a particular Gtf may be utilized.

Exemplary antibody fragments include, without limitation, Fab fragments, Fab' fragments, F(ab)$_2$ fragments, F(ab')$_2$ fragments, Fd fragments, Fv fragments, dAb fragments, and isolated complementarity determining regions ("CDRs") (see U.S. Pat. Nos. 7,037,498, 7,034,121, 7,041,870, and 7,074,405, which are hereby incorporated by reference in their entirety). These antibody fragments can be made by conventional procedures, such as proteolytic fragmentation procedures, as described in J. Goding, *Monoclonal Antibodies: Principles and Practice*, pp. 98-118 (N.Y. Academic Press 1983), which is hereby incorporated by reference in its entirety.

Alternatively, the processes of the present invention can utilize probes found either in nature or prepared synthetically by recombinant DNA procedures or other biological or molecular procedures. Suitable probes are molecules that bind specifically to a glucosyltransferase identified by the monoclonal antibodies of the present invention. Such probes can be, for example, proteins, peptides, lectins, or nucleic acid probes.

Exemplary peptides include polypeptide monobodies which can be prepared as described in U.S. Pat. No. 6,673,901 to Koide et al. and U.S. patent application Ser. No. 10/006, 760 to Koide, each of which is hereby incorporated by reference in its entirety, and then screened for Gtf binding by yeast-two hybrid screening of the peptide library. Once identified, the monobodies can be employed in the detection procedures employed herein.

Exemplary nucleic acids include nucleic aptamers such as the dimeric or di-dimeric or multimeric aptamers described in U.S. Pat. No. 6,458,559 to Shi et al. and U.S. Patent Publication No. 2005/0282190 to Shi et al., each of which is hereby incorporated by reference in its entirety. Methods of making bivalent and multivalent aptamers and their expression in multi-cellular organisms are described in U.S. Pat. No. 6,458, 559 to Shi et al., which is hereby incorporated by reference in its entirety. A method for modular design and construction of multivalent nucleic acid aptamers, their expression, and methods of use are also described in U.S. Patent Publication No. 2005/0282190, which is hereby incorporated by reference in its entirety.

Identifying suitable nucleic acid aptamers that bind to a particular Gtf basically involves selecting aptamers that bind Gtf with sufficiently high affinity (e.g., $K_d$=20-50 nM) and specificity from a pool of nucleic acids containing a random region of varying or predetermined length (Shi et al., "A Specific RNA Hairpin Loop Structure Binds the RNA Recognition Motifs of the Drosophila SR Protein B52," *Mol. Cell Biol.* 17:1649-1657 (1997); Shi, "Perturbing Protein Function with RNA Aptamers" (thesis, Cornell University) microformed on (University Microfilms, Inc. 1997), which are hereby incorporated by reference in their entirety). Aptamers may be identified that bind exclusively to a single Gtf target or to multiple Gtf targets. For example, identifying suitable nucleic acid aptamers can be carried out using an established in vitro selection and amplification scheme known as SELEX. The SELEX scheme is described in detail in U.S. Pat. No. 5,270,163 to Gold et al.; Ellington and Szostak, "In Vitro Selection of RNA Molecules that Bind Specific Ligands," *Nature* 346:818-822 (1990); and Tuerk & Gold, "Systematic Evolution of Ligands by Exponential Enrichment: RNA Ligands to Bacteriophage T4 DNA Polymerase," *Science* 249:505-510 (1990), which are hereby incorporated by reference in their entirety. The SELEX procedure can be modified so that an entire pool of aptamers with binding affinity can be identified by selectively partitioning the pool of aptamers. This procedure is described in U.S. Patent Application Publication No. 2004/0053310 to Shi et al., which is hereby incorporated by reference in its entirety. Having identified individual aptamer sequences having specificity for one or more Gtfs, the aptamers can then be assembled into the multimeric forms described above.

It is particularly preferred to use the monoclonal antibodies or their binding fragments identified as glucosyltransferase-specific antibodies. These antibodies can be used alone or as a component in a series or mixture with other antibodies or other biological agents.

A second aspect of the present invention relates to an immunological kit for detecting a glucosyltransferase enzyme in an oral sample obtained from an animal. The kit includes an antibody or antibody fragment or other probe that specifically binds to a glucosyltransferase enzyme, preferably those described above. In certain embodiments, the antibody or antibody fragment or other probe and can be directly labeled with a detectable signal. In other embodiments, a secondary antibody or antibody fragment or probe that is directly labeled with the detectable signal can be used to identify presence of the (primary) antibody or antibody fragment or probe that recognizes the Gtf. The kit further includes a reaction platform for contacting the antibody or antibody fragment or probe to the oral sample. The kit can utilize any suitable detection techniques described below, but preferably an ELISA using monoclonal or monospecific antibodies to GtfB, C, or D or other Gtf of cariogenic *Streptococci*, e.g., GtfSs, as detection/prediction agents. The kit can be a rapid, reliable, and suitable test for use in healthcare offices, much like a pregnancy test.

The oral sample (e.g., saliva, oral surface (tooth or mucosa) scrapings, and dental appliance scrapings) to be analyzed will generally include those which are known, or suspected, to contain the particular glucosyltransferase enzyme. The oral sample can be obtained from any animal being tested, but preferably the animal is a mammal such as human. Even more preferably, the human is a child, most preferably under the age of 8 or 6 or 4 or 3 or 2.

The reaction platform can be any suitable solid phase support, described hereinafter.

The kit can further include one or more of ancillary materials required for use of the label (i.e., to yield a detectable signal), a control antibody, a predetermined amount of one or more Gtf enzymes and one or more suitable buffers as a diluent or wash. Where multiple antibodies or antibody fragments or probes are used (i.e., to detect different Gtfs), the kit can either contain different wells for each detection procedure or different labels will be used so that the presence of different Gtf targets can be discriminated when they are present in a single well.

A third aspect of the present invention relates to a method of detecting a glucosyltransferase enzyme in an oral sample. This method involves providing an antibody or binding portion thereof or probe that specifically binds to a glucosyltransferase enzyme. The antibody or binding portion thereof or probe is contacted with an oral sample under conditions effective to yield a detectable signal if the glucosyltransferase enzyme is present in the oral sample (i.e., if the antibody or binding portion thereof or probe binds to at least a portion of the glucosyltransferase enzyme). A determination is then made as to whether the sample yields the detectable signal, where the presence of the detectable signal indicates that the oral sample contains the glucosyltransferase enzyme. Suitable detectable signals can include, for example, an immunochemical signal, a fluorescent signal, a radioactive signal, a nuclear magnetic resonance active signal, a luminescent signal, and/or a chromophore signal.

As demonstrated herein, the detection of Gtfs in an oral sample is useful to determine whether aberrant levels of the Gtf enzyme(s) are present and/or for the presence of abnormal forms of such Gtf enzymes. By "aberrant levels" is meant higher or lower levels, but typically higher, of a Gtf enzyme relative to that present, or a standard level representing that present, in an analogous sample from a subject not having caries (e.g., early childhood caries).

A fourth aspect of the present invention relates to a method of diagnosing predisposition of a human child to early childhood caries. This method involves performing the method of the third aspect of the invention using an oral sample from a human child, where the presence of the detectable signal indicates that the sample contains the glucosyltransferase enzyme and that the human child is predisposed to early childhood caries.

In a preferred aspect, the invention provides a method of diagnosing or screening for the presence of glucosyltransferase, characterized by the presence of a glucosyltransferase antigen, comprising measuring in a subject the level of immunospecific binding of an antibody or fragment thereof to an oral sample derived from the subject, in which said antibody immunospecifically binds said antigen. An increase in the level of said immunospecific binding, relative to the level of said immunospecific binding in an analogous sample from a subject not having caries (e.g., early childhood caries), will indicate the presence of a caries favorable oral environment.

The measurement of a glucosyltransferase that is bound by an antibody can be valuable in detecting and/or staging diseases related to the molecule in a subject, in screening of such diseases in a population, in differential diagnosis of the physiological condition of a subject, and in monitoring the effect of a therapeutic treatment on a subject.

Examples of suitable assays to detect the presence of glucosyltransferase include but are not limited to ELISA, radioimmunoassay, gel-diffusion precipitation reaction assay, immunodiffusion assay, agglutination assay, fluorescent immunoassay, protein A immunoassay, or immunoelectrophoresis assay.

In performing the assays of the present invention, the assay can be performed directly on an oral sample or partially purified protein obtained therefrom. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y., which is hereby incorporated by reference in its entirety).

Immunoassays for the particular Gtf enzyme will typically comprise incubating an oral sample or partially purified protein, such as those described above, in the presence of a detectably labeled antibody and detecting the bound antibody by any of a number of techniques well-known in the art.

The oral sample may be brought into contact with and immobilized onto a solid phase support or carrier such as nitrocellulose, or other solid support which is capable of immobilizing cells, cell particles or soluble or insoluble proteins. The support may then be washed with suitable buffers followed by treatment with the detectably labeled antibody. The solid phase support may then be washed with the buffer a second time to remove unbound antibody. The amount of bound label on solid support may then be detected by conventional means.

"Solid phase support or carrier" includes any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Those skilled in the art will know many other suitable carriers for binding antibody or antigen, or will be able to ascertain the same by use of routine experimentation.

The binding activity of a given antibody or antibody fragment or probe may be determined according to well known methods. Those skilled in the art will be able to determine operative and optimal assay conditions for each determination by employing routine experimentation.

One of the ways in which an antibody or antibody fragment or probe can be detectably labeled is by linking the same to an enzyme and using the antibody in an enzyme immunoassay (EIA) (Voller, "The Enzyme Linked Immunosorbent Assay (ELISA)", Diagnostic Horizons 2:1-7, Microbiological Associates Quarterly Publication, Walkersville, Md. (1978); Voller et al., *J. Clin. Pathol.* 31:507-520 (1978); Butler, *Meth. Enzymol.* 73:482-523 (1981); Maggio, E. (ed.), *Enzyme Immunoassay*, CRC Press, Boca Raton, Fla. (1980); Ishikawa et al., (eds.), *Enzyme Immunoassay*, Kgaku Shoin, Tokyo (1981)), which are hereby incorporated by reference in their entirety). The enzyme which is bound to the antibody or antibody fragment or probe will react with an appropriate substrate, preferably a chromogenic substrate, in such a manner as to produce a chemical moiety which can be detected, for example, by spectrophotometric, fluorimetric or by visual means. Enzymes that can be used to detectably label the antibody or antibody fragment or probe include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibody or antibody fragment or probe, it is possible to detect the protein that the antibody or antibody fragment or probe was designed for through the use of a radioimmunoassay (RIA) (see, e.g., Weintraub, *Principles of Radioimmunoassays*, Seventh Training Course on Radioligand Assay Techniques, The Endocrine Society (1986), which is hereby incorporated by reference in its entirety). The radioactive isotope can be detected by such means as the use of a gamma counter or a scintillation counter or by autoradiography.

It is also possible to label the antibody or antibody fragment or probe with a fluorescent compound. When the fluorescently labeled antibody or antibody fragment or probe is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody or antibody fragment or probe can also be detectably labeled using fluorescence emitting metals such as $^{152}Eu$, or others of the lanthanide series. These metals can be attached to the antibody or antibody fragment or probe using such metal chelating groups as diethylenetriaminepentacetic acid (DTPA) or ethylenediaminetetraacetic acid (EDTA).

The antibody or antibody fragment or probe also can be detectably labeled by coupling it to a chemiluminescent compound. The presence of the chemiluminescent-tagged antibody or antibody fragment or probe is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody or antibody fragment or probe of the present invention. Bioluminescence is a type of chemiluminescence found in biological systems, in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

One embodiment of the detection method of the present invention is described below, and is based on the correlation between Gtf activity and caries experience. The method, in application, will be a quick, reliable test to predict caries. The method includes a type of dip test involving saliva or other oral samples (described above) that will be rapidly collected in the practitioner's office (e.g., dentist or primary care physician or other clinician). Because the collection of plaque is time consuming and may hinder the rapidity of which the test could be performed, saliva is the preferred sample.

In another embodiment, the test kit utilizes the principle of ELISA using one or more monoclonal antibodies to GtfB, C, or D or other Gtf of cariogenic *Streptococci* as detection/prediction agents. A monoclonal antibody to GtfB is most preferred. This test kit also contains a polystyrene plate with reaction wells. In the test, subject saliva can be mixed in a 1:1 ratio with a buffer supplied in the kit and then coated onto the wells of the polystyrene plates. After the plates are coated, they will be washed with washing buffer. The wells, which will have constituents of saliva coated on them, will then be exposed to blocking buffer and will then be washed with washing buffer. Next, a primary, monoclonal antibody raised to GtfB and, optionally, one or more additional monoclonal antibodies to GtfC, GtfD, or Gtf of *S. sanguis* (e.g., GtfSs), prepared in double dilution in blocking buffer, will be added to separate wells or, if distinctly labeled, the same well. After exposure, the wells will be washed and exposed to a secondary antibody, labeled with alkaline phosphatase, and prepared in blocking buffer. This antibody will react with the monoclonal antibody. After incubation, the wells will be washed and developed with para-nitro-phenylphosphate substrate that reacts with the alkaline-phosphatase. Controls will include wells that do not contain saliva and wells that do not contain saliva but do contain known concentrations of purified GtfB, GtfC, GtfD or Gtf of *S. sanguis* (GtfSs). A positive reaction will be determined by color development, i.e., presence of color in the well indicates presence of Gtf in the saliva. It is estimated this process will take approximately one hour.

In a further embodiment, the test kit includes a test card, about the size of a credit card, with one or more indicator strips and at least six wells. The indicator strip is coated with antibody to capture any Gtf in saliva. This capture antibody can be specific for the target Gtf or capable of recognizing any Gtf. The strip will be dipped into saliva, which after collection will be placed in the first well of the card, to "catch" the Gtf in the saliva (if present). After the Gtf is captured onto the strip, the strip will then be dipped in the second well of the card, which contains an antibody specific to the target Gtf (to GtfB, C, D or Gtf of *S. sanguis* (GtfSs)) labeled with one of the above-identified enzymes (e.g., alkaline phosphatase). The antibody will react with any captured Gtf on the strip. After the reaction, the strip will be dipped into the third well, which contains para-nitro-phenyl phosphate substrate. The alkaline phosphatase of the second antibody, bound to any Gtf captured by the first antibody, will react with the substrate, resulting in a blue color development. Lack of color development will indicate absence of Gtf. The test card will come equipped with a positive control, a second strip containing Gtf, which will be processed through parallel wells (the remaining three wells). This three-step test will produce results in about thirty minutes. Each test kit of this type can be specific for a single Gtf target. Alternatively, the kit can be provided with multiple indicator strips and wells for each target Gtf, i.e., one test strip, one control strip, and six wells for each of GtfB, C, and D (total of six strips and 18 wells).

Another embodiment of the kit includes one or more indicator strips that, upon reaction with saliva, will change color to indicate the presence of a target Gtf in the saliva. Each kit preferably contains separate indicator strips for each Gtf target or distinct regions of a single indicator strip, where each region is specific for a particular Gtf target. The results from this test will be produced in a matter of minutes, e.g., about ten minutes, and will be detectable to the naked eye.

From the foregoing, it should be appreciated that the methods of the present invention can be used to identify those subjects likely to develop carious lesions and to predict caries activity before lesions develop. Such a test can be used in dental practice to identify patients at risk for development of dental caries. Patients identified as at-risk for the development of dental caries could then be given appropriate preventive counseling/treatment, and the method subsequently can be used to monitor effectiveness.

The antibodies (or functionally active fragments thereof) useful in the present invention may, additionally, be employed histologically, as in immunofluorescence, immunohistochemistry, or immunoelectron microscopy, for in situ detection of the Gtf enzyme. In situ detection may be accomplished by removing a histological specimen from a patient and applying thereto a labeled antibody of the present invention. The antibody (or functionally active fragment thereof) is preferably applied by overlaying the labeled antibody onto an oral sample. Using the present invention, those of ordinary skill will readily perceive that any of a wide variety of histological methods (such as staining procedures) can be modified in order to achieve such in situ detection of glucosyltransferase.

EXAMPLES

The following examples are intended to illustrate embodiments of the present invention but they are by no means intended to limit the scope of the present invention.

Example 1

Studies to Determine Correlation Between Quantities of Gtf Enzymes in Saliva and the Number of Carious Lesions Experimental investigations were performed to determine whether the quantities of GtfB, GtfC, or GtfD, and/or overall Gtf activity in young subject saliva correlates with the number of carious lesions. Such investigations were helpful in developing a simple calorimetric test for caries activity, based on monoclonal antibody to Gtf, which can be used by dentists in their office.

Gtf has been chosen as a marker for caries activity for several reasons.

First, Gtf is a proven virulence factor in the pathogenesis of dental caries (Yamashita et al., "Role of the *Streptococcus mutans* gtf Genes in Caries Induction on the Specific-Pathogen-Free Rat Model," *Infect Immun* 61:3811-3817 (1993), which is hereby incorporated by reference in its entirety).

Second, Gtf has been identified in salivary pellicle (Rolla et al., "Identification of IgA, IgG, Lysozyme, Albumin, Amylase and Glucosyltransferase in the Protein Layer Adsorbed to Hydroxyapatite from Whole Saliva," *Scand J Dent Res* 91:186-190 (1983), which is hereby incorporated by reference in its entirety).

Third, Gtf participates in the colonization of the tooth surface by bacteria by synthesizing glucan, which contributes to the bulk of dental plaque (Critchley, "The Breakdown of the Carbohydrate and Protein Matrix of Dental Plaque," *Caries Res* 3:249-265 (1969); Critchley, "The Microbiology of Dental Plaque with Special Reference to Polysaccharide Formation," *Dtsh Zah Zeitschrift* 26:1155-1161 (1971); Critchley et al., "The Polymerisation of Dietary Sugars by Dental Plaque," *Caries Res* 1:112-129 (1967); Critchley et al., "The Histology and Histochemistry of Dental Plaque," *Caries Res* 2:115-129 (1968); Hamada et al., "Biology, Immunology, and Cariogenicity of *Streptococcus mutans*," *Microbiol Rev* 44:331-384 (1980); Wood et al., "The Extracellular Polysaccharide Produced from Sucrose by Cariogenic Streptococcus," *Archs Oral Biol* 11: 1039-1042 (1968), which are hereby incorporated by reference in their entirety).

Fourth, Gtf and the glucan synthesized by the Gtf enzymes contribute to the virulence of mutans streptococci in dental caries (Krasse, "The Effects of Caries-Inducing Streptococci in Hamsters Fed Diets with Sucrose or Glucose," *Arch Oral Biol* 10:223-226 (1965); Hamada et al., "Biology, Immunology, and Cariogenicity of *Streptococcus mutans*," *Microbiol Rev* 44:331-384 (1980); Curtiss et al., "Analysis of *Streptococcus mutans* Virulence Attributes Using Recombinant DNA and Immunological Techniques," in *Glucosyltransferases, Sucrose, and Dental Caries*, Doyle et al., eds., Spec. Suppl. Chemical Senses, Washington, D.C.: IRL Press, pp. 95-104 (1983); Hamada et al., "Virulence Factors of *Streptococcus mutans* and Dental Caries Prevention," *J Dent Res* 63:407-411 (1984); Tanzer et al., "Virulence of Mutants Defective in Glucosyltransferase, Dextran-Meditated Aggregation, or Dextranase Activity, in *Molecular Basis of Oral Microbial Adhesion*, Mergenhagen et al., eds., Washington, D.C.: American Society for Microbiology, pp. 204-211 (1985); Koga et al., "Adherence of *Streptococcus mutans* to Tooth Surfaces, in *Molecular Microbiology and Immunology of Streptococcus mutans*," Hamada et al., eds., Amsterdam: Elsevier Science Publishers, pp. 133-143 (1985); Loesche, "Role of *Streptococcus mutans* in Human Dental Decay," *Microbiol Rev* 50:353-380 (1986); Drake et al., "Specificity of the Glucan-Binding Lectin of *Streptococcus cricetus*," *Infect Immun* 56:1864-1872 (1988); Kuramitsu, "Virulence Factors of Mutans Streptococci: Role of Molecular Genetics," *Crit Rev Oral Biol Med* 4:159-176 (1993), which are hereby incorporated by reference in their entirety).

Numerous studies have been carried out involving glucosyltransferases from mutans streptococci. For example, assays for Gtf in whole human saliva from several donors both in solution and when adsorbed onto sHA beads revealed that salivary Gtf has properties similar to those of GtfC (Vacca Smith et al., "Characterization of Glucosyltransferase of Human Saliva Adsorbed onto Hydroxyapatite Surfaces,"

*Caries Res* 30:354-360 (1996), which is hereby incorporated by reference in its entirety). Briefly, in that study, the activities of GtfB, GtfC and GtfD, adsorbed onto sHA, were compared with those of Gtfs of donor whole saliva. Antiserum raised against a mixture of the three Gtfs was found to reduce the activity of GtfB only, and had no effect on Gtf activities of the donor salivas. GtfB, and not the Gtfs of the saliva of the donors, was found to be stimulated in the presence of starch hydrolysates. GtfC and GtfD activities were found to be enhanced on the surfaces, as were the Gtf activities of donor saliva. The activities of GtfB and GtfD, but not GtfC, were found to be stimulated by dextran. The Gtf activities of donor salivas were found to be unaffected by dextran. Therefore, Gtf activity in pellicles was determined to have properties similar to those of GtfC.

These data are supported by results indicating that GtfC has high affinity for hydroxyapatite and saliva-coated hydroxyapatite surfaces, while GtfB binds avidly to bacterial surfaces in an active form (Vacca Smith et al., "Binding Properties of Streptococcal Glucosyltransferases for Hydroxyapatite, saliva-coated Hydroxyapatite, and Bacterial Surfaces," *Archs Oral Biol* 43:103-110 (1998), which is hereby incorporated by reference in its entirety). Thus it appears that Gtf enzymes (B, C, and D), although they share a common substrate, play distinct roles in plaque and biofilm formation.

Salivary Gtf in situ was also studied using hydroxyapatite discs placed in the mouth (Vacca Smith et al., "In situ Studies of Pellicle Formation on Hydroxyapatite Discs," *Archs Oral Biol* 45:277-291 (2000), which is hereby incorporated by reference in its entirety). Direct assay of the disc placed in the mouth for glucosyltransferase revealed that Gtf can be incorporated into a salivary pellicle within a matter of minutes.

A large volume of data has been generated concerning the binding specificities of Gtf enzymes to saliva-coated hydroxyapatite beads and to bacterial surfaces (Vacca Smith et al., "Binding Properties of Streptococcal Glucosyltransferases for Hydroxyapatite, saliva-coated Hydroxyapatite, and Bacterial Surfaces," *Archs Oral Biol* 43:103-110 (1998), which is hereby incorporated by reference in its entirety).

For hydroxyapatite (HA) beads, the following values were obtained (K=affinity; N=number of binding sites): GtfB, K=46×10$^5$ ml/μmol, N=0.65×10$^{-6}$ μmol/m2; GtfC, K=86×10$^5$ ml/μmol, N=4.42×10$^{-6}$ μmol/m2; and GtfD, K=100×10$^5$ ml/μmol, N=0.83×10$^{-6}$ μmol/m$^2$ (Vacca Smith et al., "Binding Properties of Streptococcal Glucosyltransferases for Hydroxyapatite, saliva-coated Hydroxyapatite, and Bacterial Surfaces," *Archs Oral Biol* 43:103-110 (1998), which is hereby incorporated by reference in its entirety).

For sHA beads, the following numbers were obtained: GtfB, K=14.7×10$^5$ ml/μmol, N=1.03×10$^{-6}$ μmol/m$^2$; GtfC, K=21.3×10$^5$ ml/μmol, N=3.66×10$^{-6}$ μmol/m$^2$; GtfD, K=1.73×10$^5$ ml/μmol, N=8.88×10$^{-6}$ μmol/m$^2$ (Vacca Smith et al., "Binding Properties of Streptococcal Glucosyltransferases for Hydroxyapatite, saliva-coated Hydroxyapatite, and Bacterial Surfaces," *Archs Oral Biol* 43:103-110 (1998), which is hereby incorporated by reference in its entirety).

Thus, GtfC was found to have the highest affinity for sHA beads, and GtfB was found to bind with high affinity to sHA as well. The binding of GtfB to sHA in the presence of parotid saliva supplemented with GtfC and GtfD was reduced when compared with its binding to sHA in the presence of parotid saliva alone (Vacca Smith et al., "Binding Properties of Streptococcal Glucosyltransferases for Hydroxyapatite, Saliva-coated Hydroxyapatite, and Bacterial Surfaces," *Archs Oral Biol* 43:103-110 (1998), which is hereby incorporated by reference in its entirety). In contrast, the binding of GtfC and D to sHA was unaffected when parotid saliva was supplemented with the other Gtf Enzymes (Vacca Smith et al., "Binding Properties of Streptococcal Glucosyltransferases for Hydroxyapatite, Saliva-coated Hydroxyapatite, and Bacterial Surfaces," *Archs Oral Biol* 43:103-110 (1998), which is hereby incorporated by reference in its entirety).

GtfB bound to several bacterial strains (*S. mutans* GS-5, *Actinomyces viscosus* OMZ105E, and *Lactobacillus casei* 4646) in an active form, while GtfC and GtfD did not bind to bacterial surfaces (Vacca Smith et al., "Binding Properties of Streptococcal Glucosyltransferases for Hydroxyapatite, Saliva-coated Hydroxyapatite, and Bacterial Surfaces," *Archs Oral Biol* 43:103-110 (1998), which is hereby incorporated by reference in its entirety). It was concluded that of the three Gtf enzymes, GtfC has the highest affinity for HA and sHA surfaces and can adsorb on to the sHA surface in the presence of the other two enzymes, that GtfB can bind to both sHA and bacterial surfaces, and that GtfD does not seem to bind well to either sHA or bacterial surfaces (Vacca Smith et al., "Binding Properties of Streptococcal Glucosyltransferases for Hydroxyapatite, saliva-coated Hydroxyapatite, and Bacterial Surfaces," *Archs Oral Biol* 43:103-110 (1998), which is hereby incorporated by reference in its entirety).

Studies have shown that the different Gtf enzymes interact with salivary components such as α-amylase both in solution and on sHA, and that glucan production by GtfB on sHA beads is stimulated in the presence of starch hydrolysates, which results in the synthesis a novel glucan that promotes the adherence of bacteria that normally don't bind to glucan (Vacca Smith et al., "Interactions of Streptococcal Glucosyltransferases with α-Amylase and Starch on the Surface of Saliva-Coated Hydroxyapatite," *Archs Oral Biol* 30:291-298 (1996); Kopec et al., "Structural Aspects of Glucans Formed in Solution and on the Surface of Saliva-Coated Hydroxyapatite," *Glycobiology* 7:929-934 (1997), which are hereby incorporated by reference in their entirety).

Further, results have indicated that conformational changes might occur within the enzymes when adsorbed onto saliva-coated hydroxyapatite (sHA) beads. For example, Gtf enzymes, when adsorbed onto sHA, are active over broad pH and temperature ranges when compared with activities in solution (Schilling et al., "Adherence of *Streptococcus mutans* to Glucans Formed in situ in Salivary Pellicle.," *J Dent Res* 68:678-1680 (Special Issue) (1989), which is hereby incorporated by reference in its entirety), where enzymes are active only over narrow pH and temperature ranges, and the K$_m$ values for sucrose for all three enzymes are lower when the enzyme was adsorbed to a surface, than when in solution (Venkitaraman et al., "Characterization of GlucosyltransferaseB, GtfC, and GtfD in Solution and on the Surface of Hydroxyapatite," *J Dent Res* 74:1695-1701 (1995), which is hereby incorporated by reference in its entirety). Finally, the Gtf enzymes form structurally distinct glucans on a surface (Kopec et al., "Structural Aspects of Glucans Formed in Solution and on the Surface of Saliva-Coated Hydroxyapatite," *Glycobiology* 7:929-934 (1997), which is hereby incorporated by reference in its entirety).

It has been determined that whole saliva contains many proteases that could affect Gtf activity. To determine the ability of Gtf to remain active in the milieu of saliva, saliva was supplemented with Gtf and tested for activity of the exogenous Gtf. Briefly, Gtf enzymes, mixed with either buffer or clarified whole saliva, or clarified whole saliva mixed with buffer (control for endogenous Gtf of saliva), were exposed immediately after mixture to radioactive sucrose (labeled in glucose moiety) substrate. After incubation with sucrose, the amount of radioactive-glucose incorporated into glucan was determined according to previously described methods (Schilling et al., "The Activity of Glucosyltransferases Adsorbed onto Saliva-Coated Hydroxyapatite," *J Dent Res* 67:2-8 (1988), which is hereby incorporated by reference in its entirety). Additional control samples contained buffer alone. It can be seen in FIG. 1 that naturally occurring Gtf activity can be detected in whole saliva by direct enzyme assay, and that exogenous Gtf enzymes are active in the milieu of whole saliva. Therefore, Gtfs appear to display remarkable stability in whole saliva despite the presence of a myriad of proteases.

Example 2

Studies Involving Polyclonal Antiserum Raised to GtfC

Figure 2:
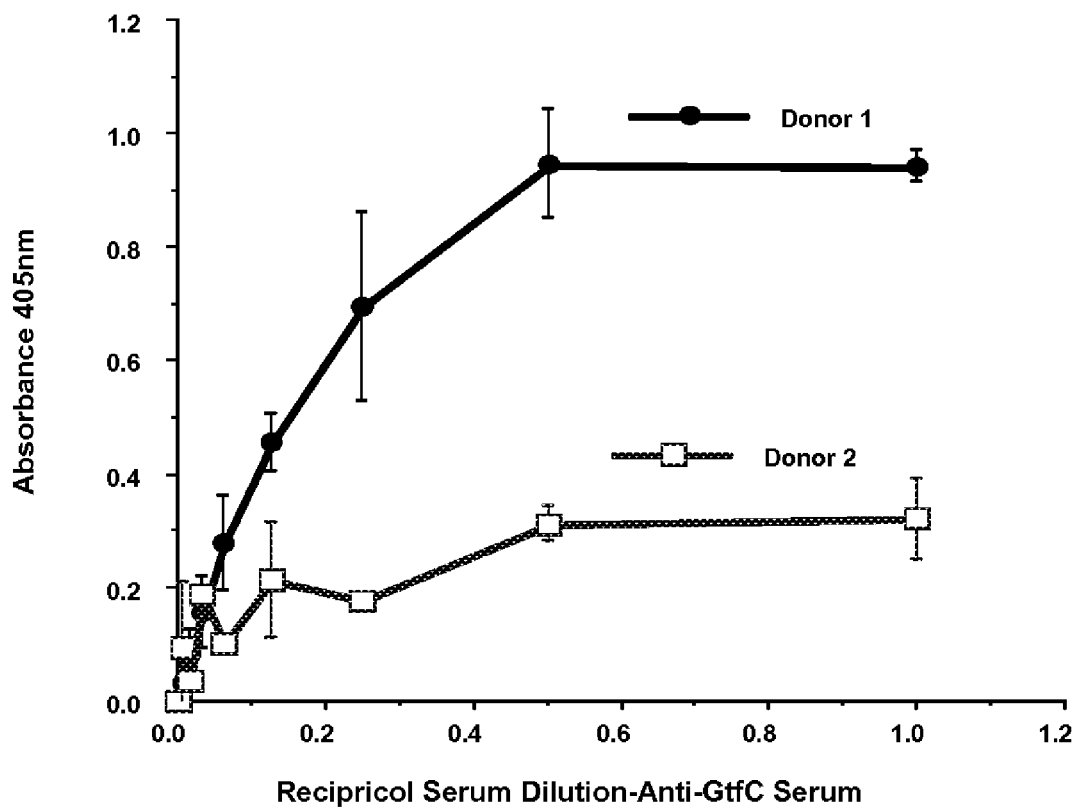
FIG. 2 is a line graph showing the detection of GtfC in human saliva by ELISA using polyclonal antiserum.

Gtf was detected in clarified whole human saliva by using ELISA using polyclonal antiserum raised to GtfC (FIG. 2). GtfC was focused on since the preliminary data indicated that Gtf activity found in whole saliva has properties of GtfC prepared from mutans streptococci (Vacca Smith et al., "Characterization of Glucosyltransferase of Human Saliva Adsorbed onto Hydroxyapatite Surfaces," *Caries Res* 30:354-360 (1996), which is hereby incorporated by reference in its entirety). It was found that saliva with high Gtf activity (Donor 1), as determined by direct activity assay (2.0 units of activity/milliliter of saliva), reacts with antiserum specific for GtfC, while saliva with low Gtf activity (Donor 2), as determined by direct activity assay (0.65 units of activity/milliliter of saliva), does not react with the antiserum as shown below in FIG. 2. For these experiments, a unit of Gtf activity was defined as that amount of Gtf required to incorporate 1000 units of radioactive glucose into glucan over a 4 hour time period. It is interesting to note that Donor 1, who had high salivary Gtf activity and whose saliva showed high reactivity with antiserum specific for GtfC by ELISA assay, also had high caries activity, whereas Donor 2, who had low salivary Gtf activity and whose saliva did not react with antiserum to GtfC by ELISA assay, had low caries activity.

Example 3

Figure 3:
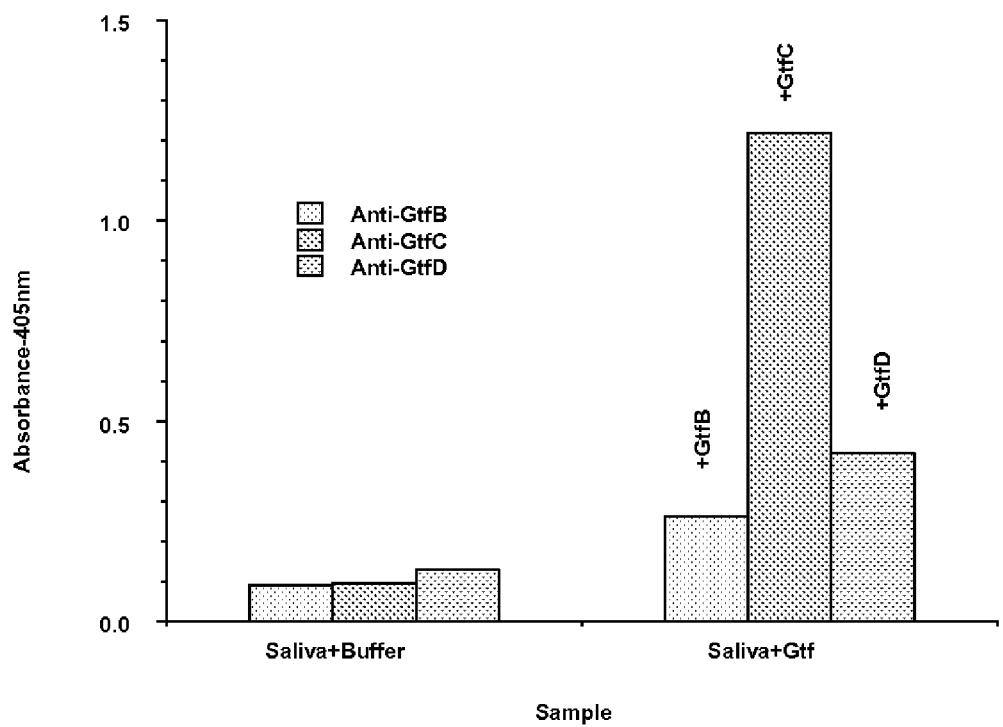
FIG. 3 is a bar graph showing the detection of natural and exogenous Gtf in whole human saliva by monospecific antisera.

Studies Using Polyclonal Sera Rendered Monospecific to a Particular Target Gtf Enzyme ELISA assays were also performed using polyclonal sera rendered monospecific to particular target Gtf enzyme, as shown in FIG. 3. The polyclonal sera raised to GtfB, GtfC, or GtfD were made monospecific for their target Gtfs by exposing these antisera to hydroxyapatite beads coated with non-target Gtfs, thereby removing antibodies cross-reactive to non-target Gtf enzyme. Monospecificity was determined by ELISA assay. To determine the ability of the monospecific antisera to recognize endogenous Gtf in clarified whole human saliva, and to recognize exogenous target Gtf added to such saliva, clarified whole human saliva was mixed with either buffer, GtfB, GtfC, or Gtf D and coated onto an ELISA plate.

The samples were probed with primary antisera: either anti-GtfB sera, (for saliva alone or saliva mixed with GtfB), anti-GtfC sera (for saliva alone or saliva mixed with GtfC), or anti-GtfD sera (for saliva alone or saliva mixed with GtfD). Controls consisted of saliva/buffer or saliva/Gtf processed in the ELISA assay in the absence of primary antisera, and primary antisera exposed to plates coated with buffer alone. The absorbance values for the controls were subtracted from the appropriate experimental samples. It can be seen in FIG. 3 that the antisera recognized endogenous Gtf in clarified whole human saliva and, in addition, recognized exogenous Gtf mixed in with clarified whole human saliva. These studies also show that Gtf enzymes can bind to the ELISA plates even in a saliva environment.

Example 4

Figure 4:
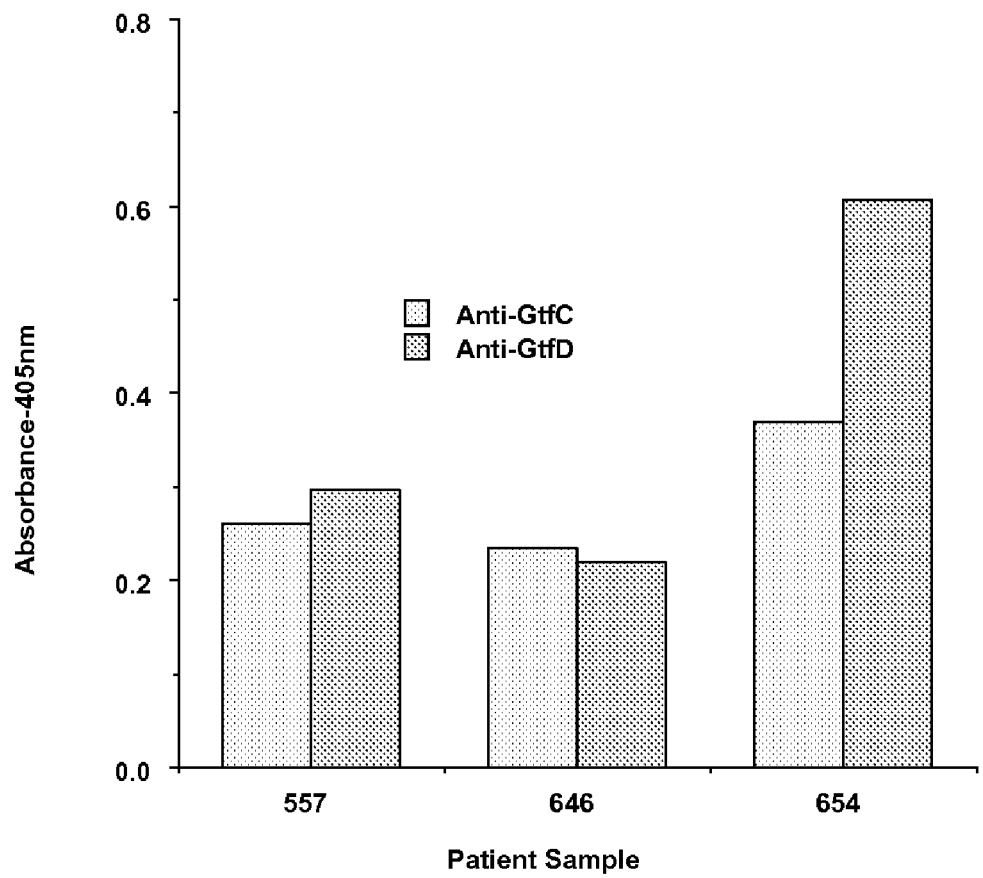
FIG. 4 is a bar graph showing the detection of Gtf in saliva of pediatric subjects by ELISA using monospecific sera (i.e., anti-GtfC and anti-GtfD).

Studies Involving Monospecific Primary Sera to Recognize Gtf in Saliva Obtained from Pediatric Subjects Preliminary studies were carried out and showed the ability of monospecific primary sera to recognize Gtf in saliva obtained from pediatric subjects, aged 11-16 years old, with unknown caries experience. Saliva from three different pediatric subjects was coated onto ELISA plates and examined for presence of Gtf enzymes by probing with sera that recognize either GtfC or GtfD. As shown in FIG. 4, GtfD was detected in some of the subjects' saliva. Controls consisted of saliva processed in the ELISA assay in the absence of primary antisera, and primary antisera exposed to samples that did not contain saliva. Absorbance values were subtracted from experimental samples.

Figure 5:
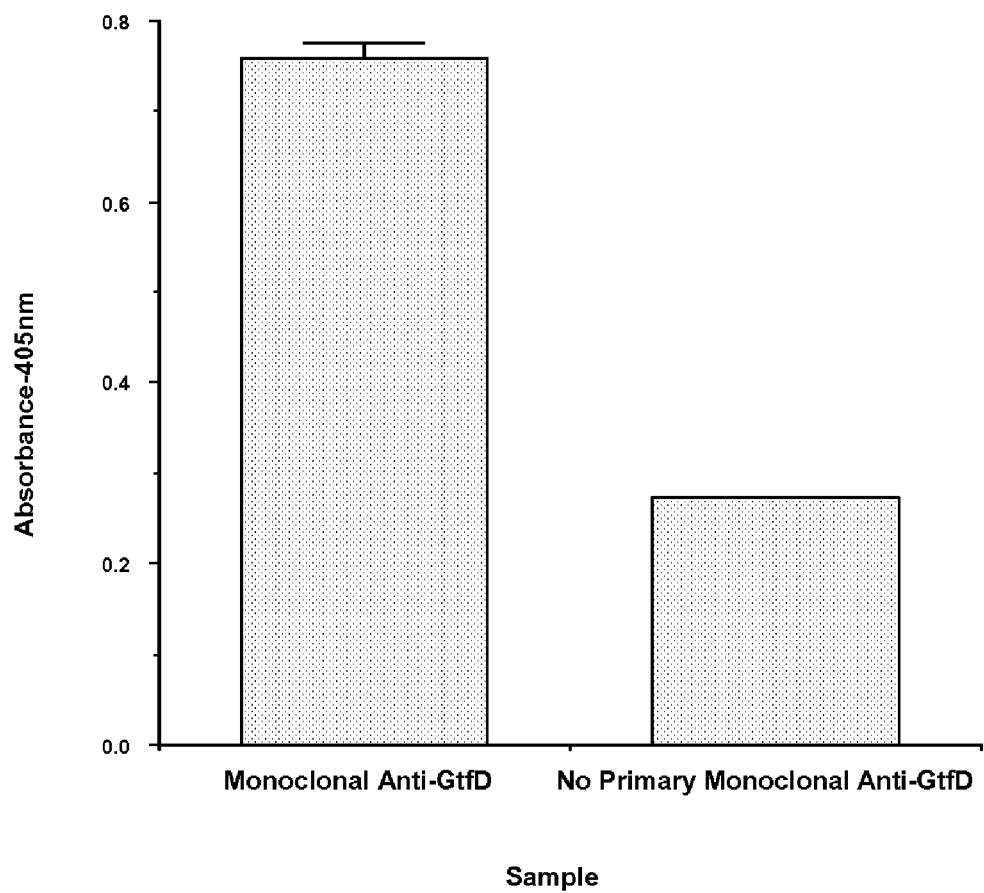
FIG. 5 is a bar graph showing the detection of Gtf in saliva of pediatric subjects using a monoclonal antibody to GtfD.

The presence of GtfD in saliva of pediatric subject 654 was confirmed using monoclonal antibody specific for GtfD. Saliva from pediatric subject 654 was coated onto ELISA plates and tested for presence of GtfD by probing with monoclonal antibody specific for GtfD, or with no antibody in control samples. As shown in FIG. 5, GtfD was detected in the subject's saliva.

Example 5

Correlation of GtfB with Caries Level (DFS) Using Logistic Regression Analyses

Studies were carried out to determine whether there was a correlation between GtfB levels and caries activity, as measured by decayed and filled surfaces in primary teeth (referred to herein and in the art as "DFS"). Saliva was collected from 21 caries-free children and from 25 caries-active children. A subject was classified as caries active if 3-4 lesions were present on free smooth surfaces including upper incisors, and patients with white spots in enamel were regarded as caries active. If such lesions were not present, the subject was classified as caries free. The saliva was coated onto ELISA plates and examined for presence of GtfB enzymes by probing with a monoclonal antibody to GtfB or with no antibody in control samples. To determine whether there was a correlation of DFS with GtfB, logistic regression analyses were performed, as described below in Tables 1-3.

TABLE 1

| Response Profile | | |
| --- | --- | --- |
| Ordered Value | DFS | Total Frequency |
| 1 | 1 | 25 |
| 2 | 0 | 21 |

Probability modeled is DFS = 1.
Number of Observations Read: 46.
Number of Observations Used: 46.

TABLE 2

Analysis of Maximum Likelihood Estimates

| Parameter | DF | Estimate | Standard Error | Wald Chi-Square | Pr > ChiSq |
|---|---|---|---|---|---|
| Intercept | 1 | −3.6214 | 1.5444 | 5.4985 | 0.0190 |
| GtfB | 1 | 2.5474 | 1.1295 | 5.0861 | 0.0241 |

Note:
GtfB correlates with DFS (p-value = 0.02). More GtfB relates to more severe caries.

TABLE 3

Result from Model Selection; Analysis of Maximum Likelihood Estimates

| Parameter | DF | Estimate | Standard Error | Wald Chi-Square | Pr > ChiSq |
|---|---|---|---|---|---|
| Intercept | 1 | −3.8702 | 1.4438 | 7.1852 | 0.0074 |
| GtfB | 1 | 2.3808 | 0.8749 | 7.4043 | 0.0065 |

Note:
GtfB correlates with DFS (p-value = 0.007). More GtfB relates to more severe caries.

From the foregoing statistical analyses, it is apparent that GtfB presence correlates with caries activity and, more specifically, the degree of GtfB correlates with severity of caries.

Materials and Methods for Examples 6 and 7

Antibodies: Polyclonal antisera to Gtfs C and D were raised in rabbits to purified GtfC or GtfD (Venkitaraman et al., "Characterization of GlucosyltransferaseB, gtfC, and gtfd in Solution and on the Surface of Hydroxyapatite," *J Dent Res* 74:1695-1701 (1995); Wunder et al., "Effects of Antibodies to Glucosyltransferase on Soluble and Insolubilized Enzymes," *Oral Dis* 6(5):289-96 (2000), which are hereby incorporated by reference in their entirety) and were made monospecific for their target Gtfs by exposing these antisera to hydroxyapatite beads coated with purified non-target Gtfs, thereby removing antibodies cross-reactive to non-target Gtf enzyme. Monospecificity of antibodies in the antisera was determined by ELISA assay (see method described below) using purified GtfB, GtfC, and GtfD as target antigens. ELISA and western blot assays were also performed to verify that the antibodies did not cross-react with salivary constituents.

Monoclonal antibody to GtfB was prepared by fusion of spleen cells from mice immunized with purified GtfB (Venkitaraman et al., "Characterization of GlucosyltransferaseB, gtfC, and gtfd in Solution and on the Surface of Hydroxyapatite," *J Dent Res* 74:1695-1701 (1995), which is hereby incorporated by reference in its entirety) with myeloma cell line (ATCCTIB-9) and cloning by limiting dilution using the techniques described by Ivanyi and Davies, "Monoclonal Antibodies Against Human Growth Hormone," *Mol Immunol* 17(2):287-90 (1980), which is hereby incorporated by reference in its entirety). Specificity of monoclonals in hybridoma cell line culture supernatant fluids was determined by ELISA assay (see method described below) using purified GtfB, GtfC, and GtfD as target antigens, and the antibody was found specific for GtfB.

All animal manipulations were performed in accordance with guidelines established by the University of Rochester Committee on Animal Research.

Dental Examination and Saliva Collection: Whole saliva was collected from 50 children, 25 of whom were caries-active and 25 who were caries free, at the time of their dental examination, age 42-60 months. Children with ECC were chosen for this study to ensure that the subjects were indeed caries-active. Human subject recruitment, consent, and saliva collection were performed in accordance to protocol approved by University of Rochester Institutional Review Board. Every subject was given a unique identifier and information about subjects was kept confidential in accordance with HIPPA regulations. Study subjects were recruited from the patient population of the Division of Pediatric Dentistry, Eastman Dental Center, University of Rochester. The criteria for establishing a diagnosis of severe ECC were carious lesions affecting at least 2 of the 4 maxillary primary incisors and 2 of the 4 buccal segments. Group A consisted of 15 males and 10 females ranging in age from 38 to 70 months (mean age 55 months). Group A ethnicity was as follows: 10 African Americans; 11 Whites; 2 Asians; 1 Hispanic; and 1 mixed racial. Group B subjects consisted of 25 children who were clinically free of caries. Group B consisted of 15 males and 10 females ranging in age from 22 to 70 months (mean age: 48 months). Group B ethnicity was as follows: 4 African Americans; 19 Caucasian; 1 Asian; and 1 Hispanic.

Caries status was evaluated by two trained and calibrated clinical examiners at the time of entry of the subjects into the study. The examiners were recalibrated every 3 months during the study period (K=1). No opportunity was provided for performing repeated evaluations on the same study subject by the same examiner and, thus, no quantitative assessment of intra-examiner reliability was calculated. A surface was declared as having carious lesions per the criteria of Radike et al., "Criteria for Diagnosing Dental Caries," pp. 87-88 In Proceedings of the Conference on Clinical Testing of Cariostatic Agents, 1968, American Dental Association, Chicago (1972), which is hereby incorporated by reference in its entirety), with the exception that white spot lesions were not penetrated with an explorer.

An unstimulated whole saliva sample was obtained from each subject. The sample was obtained through a disposable saliva ejector attached to a 15 ml sterile centrifuge tube which, in turn, was attached to a vacuum pump. Two ml of saliva was collected from each subject. Group A subjects had their saliva sample taken before their oral rehabilitation under general anesthesia and accordingly, had nothing to eat or drink for at least 8 hours prior to collection. The parents of Group B subjects were instructed to give their children no food or beverage for 2 hours prior to saliva collection.

After collection, the saliva was immediately transported on ice to the laboratory and assayed within one hour of collection.

Protein Quantitation: The saliva was clarified by centrifugation, and the amount of protein in the clarified saliva was determined by ninhydrin analyses after washing (Moore, "Amino Acid Analysis: Aqueous Dimethyl Sulfoxide as Solvent for the Ninhydrin Reaction," *J. Biol. Chem.* 243(23): 6281-6283 (1968), which is hereby incorporated by reference in its entirety). The values obtained were normalized μg of protein per ml of saliva.

Glucosyltransferase Activity: The samples were assayed for Gtf activity by direct enzyme assay (Schilling and Bowen, "The Activity of Glucosyltransferases Adsorbed onto Saliva-Coated Hydroxyapatite," *J Dent Res* 67:2-8 (1988); Schilling et al., "Glucan Synthesized in situ in Experimental Pellicle Functions as Specific Binding Sites for *Streptococcus mutans*," *Infect Immun* 60:284-295 (1992); Steinberg et al., "Adhesion of Actinomyces Isolates to Experimental Pellicle," *J Dent Res* 72:1015-1020 (1993); Venkitaraman et al., "Characterization of GlucosyltransferaseB, gtfC, and gtfd in Solution and on the Surface of Hydroxyapatite," *J Dent Res*

74:1695-1701 (1995); Vacca Smith et al., "Interactions of Streptococcal Glucosyltransferases with α-amylase and Starch on the Surface of Saliva-Coated Hydroxyapatite," *Archs Oral Biol* 30:291-298 (1996); Vacca Smith et al., "Characterization of Glucosyltransferase of Human Saliva Adsorbed onto Hydroxyapatite Surfaces," *Caries Res* 30:354-360 (1996); Kopec et al., "Structural Aspects of Glucans Formed in Solution and on the Surface of Saliva-Coated Hydroxyapatite," *Glycobiology* 7:929-934 (1997); Vacca Smith and Bowen, "Binding Properties of Streptococcal Glucosyltransferases for Hydroxyapatite, Saliva-Coated Hydroxyapatite, and Bacterial Surfaces," *Archs Oral Biol* 43:103-110 (1998); and Vacca Smith and Bowen, "In situ Studies of Pellicle Formation on Hydroxyapatite Discs," *Archs Oral Biol* 45:277-291 (2000), which are hereby incorporated by reference in their entirety). Briefly, a measured volume of clarified saliva from each subject was exposed to $^{14}$C-glucosyl-sucrose (final concentration, 100 mmol/l sucrose, 40 gmol/l dextran 9,000 in buffered-KCl, pH 6.5) for four hours, 37° C., to form glucans. Gtf activity by direct enzyme assay was expressed as gmoles of glucans formed per milliliter of saliva and also per microgram of protein.

Gtf ELISA: Specific Gtf from mutans present in the salivary samples were determined by using an ELISA kit assay obtained from Kirkegaard and Perry Laboratories (Gaithersburg, Md.), supplemented with the antibodies described above. All of the buffers and reagents, which were supplied in the kit, were prepared from the kit according to the manufacturer's instructions, and the assays were performed according to the methods outlined in the manufacturer's instructions (Voller et al., "The Enzyme-Linked Immunosorbent Assay (ELISA), a Guide with Abstracts of Microplate Applications," Dynatech Laboratories Inc. Alexandria, Va. (1979); and Clark and Engval, *Enzyme immunoassay*, CRC Press, Inc., Boca Raton, Fla. (1980), which are hereby incorporated by reference in their entirety). Clarified saliva was mixed in a 1:1 ratio with the coating buffer supplied in the kit and was coated onto 96 well plates. After the plates were coated, they were washed with ELISA-kit washing buffer. The wells, which will have constituents of saliva coated on them, were then exposed to blocking buffer supplied in the kit and were then washed with washing buffer. Next, primary, monoclonal antibody to GtfB, monospecific polyclonal antibody to GtfC or GtfD, prepared in double dilution in blocking buffer were added to the wells. After exposure, the wells were washed and exposed to a secondary antibody (supplied in the kit) labeled with alkaline phosphatase and prepared in blocking buffer at a concentration to be determined by the manufacturer's instructions (Voller et al., "The Enzyme-Linked Immunosorbent Assay (ELISA), a Guide with Abstracts of Microplate Applications," Dynatech Laboratories Inc. Alexandria, Va. (1979); and Clark and Engval, *Enzyme immunoassay*, CRC Press, Inc., Boca Raton, Fla. (1980), which are hereby incorporated by reference in their entirety). After incubation, the wells were washed and developed with para-nitro-phenylphosphate substrate, per kit instructions, and the reaction was quenched with the stop reagent supplied in the ELISA kit. Controls included wells which did not contain saliva and wells which did not contain saliva but instead contained known concentrations (1 mg of protein) of purified GtfB, GtfC, or GtfD (purified by previous methods (Venkitaraman et al., "Characterization of GlucosyltransferaseB, gtfC, and gtfd in Solution and on the Surface of Hydroxyapatite," *J Dent Res* 74:1695-1701 (1995), which is hereby incorporated by reference in its entirety). After development, the intensity of the color in the wells, which correlated to the amount of Gtf present, was read in an ELISA reader (Bio-Rad, Hercules, Calif.), and the values obtained from experimental and positive control samples were divided by values of the negative control samples to obtain an absorbance index value.

Microbiological Analyses: Levels of Streptococcus mutans in the saliva of children from both groups were determined by plating a portion of the saliva, pipetted directly from the saliva prior to clarification, on selective medium (mitis-salivarius agar+bacitracin) (Staat et al., "Inhibition of Streptococcus Mutans Strains by Different Mitis-Salivarius Agar Preparations," *J Clin Microbiol* 3(3):378-80 (1976), which is hereby incorporated by reference in its entirety) and calculating the number of colony forming units (CFU) of streptococci per ml of saliva.

Statistical Analyses: Multiple logistic regressions were used to study the effects of different predictors (Gtf levels by ELISA, Gtf enzyme activity as measured by direct enzyme assay, CFU of *S. mutans*/ml of saliva) on DFS. Here, DFS was dichotomized by caries free or not. Student t-test was used to determine whether or not differences in predictor levels between caries-free and caries-active kids were statistically significant.

Example 6

Glucosyltransferase ELISA Predicts DFS

The correlation of the levels of GtfB, GtfC, and GtfD with DFS was studied by univariate logistic regressions. The results show that GtfB levels, as measured by ELISA, correlate significantly with DFS (p-value=0.003) while GtfC and GtfD levels, as measured by ELISA, did not correlate with DFS (p-values are 0.19 and 0.29 respectively). Multiple logistic regression with GtfB also showed that GtfB is a significant predictor of DFS and that the level of GtfB, as measured by ELISA, can be used to predict whether or not a patient was caries free or caries active. Analyses by Student t-test revealed a significant difference of GtfB levels in saliva between caries-free and caries-active subjects (see summary statistics in Table 4).

TABLE 4

Summary statistics

| Variable | DFS | | NON-DFS | | p-value (t-test) |
|---|---|---|---|---|---|
| | Mean | Standard Deviation | Mean | Standard Deviation | |
| CFU | 323942 | 359229 | 46173 | 168427 | 0.0029 |
| GtfB | 2.207 | 0.9077 | 1.464 | 0.3489 | 0.0013 |
| GtfC | 1.3772 | 0.5591 | 1.1254 | 0.5221 | 0.1364 |
| GtfD | 1.701 | 0.7893 | 1.7535 | 1.0921 | 0.8561 |
| Gtf Act* | 1.1159 | 0.4592 | 0.9712 | 0.6364 | 0.4072 |
| Gtf Act$ | 0.0014 | 0.0018 | 0.0017 | 0.0021 | 0.5365 |
| Protein/ml | 1306.5 | 317.1 | 1247.9 | 353.9 | 0.5701 |

To compare the accuracy of the above-identified ELISA assay to a direct enzyme assay, it was also determined whether the Gtf activity, as measured by direct enzyme assay, in the saliva of caries-free children and children with severe caries correlated with caries experience. Gtf activity was measured by direct enzyme assay as described above. The data obtained were normalized and expressed as gmoles of glucose incorporated into glucan/ml of saliva and gmoles of glucose incorporated into glucan per μg of protein. Logistic regression analysis showed Gtf activity as measured by direct enzyme assay did not correlate with DFS values (p-value=0.46 for data values normalized to volume of saliva and p-value=0.93 for data values normalized to protein content of saliva).

Example 7

Comparison of Caries Free and Severe Caries Children

DFS were determined on 50 children, 25 of whom were caries free and 25 of whom had severe caries. The mean DFS of the children with severe caries was 18.72±9 (SD).

It was determined whether a correlation existed between colony forming units (CFU) of *S. mutans* per ml of saliva and caries experience of the subjects by logistic regression of dichotomized DFS on CFU. Saliva from caries free children and children with severe caries were grown on mitis-salivarius agar with bacitracin and CFU/ml of saliva were determined. The result shows a very significant correlation of CFU with DFS (p-value=0.01).

Protein content of saliva from caries-free children and children with severe caries was determined and normalized to ml of saliva. No correlation existed between protein content of the saliva and caries experience.

Discussion of Examples 6 and 7

As shown in Examples 6 and 7, a study was executed to determine whether one could correlate the quantities of GtfB, GtfC, or GtfD, and/or Gtf activity as determined by direct enzyme assay, in the saliva of young subjects with the number of overt carious lesions and white spots.

The rationale for choosing Gtf as a marker for caries is well-founded. Results from early studies in rats infected with chemically-induced mutant strains of streptococci deficient in glucan production showed decreased cariogenicity in mutant vs. parent strains (DeStoppelaar et al., "Decrease in Cariogenicity of a Mutant of *Streptococcus Mutans*," *Archs Oral Biol* 16:971-975 (1971), which is hereby incorporated by reference in its entirety), and mutant strains of *S. mutans* defective in Gtf genes displayed reduced virulence as shown by lower number of smooth-surface carious lesions when compared to that of the wild-type parental organism (Yamashita et al., "Role of the *Streptococcus Mutans* gtf Genes in Caries Induction on the Specific-Pathogen-Free Rat Model," *Infect Immun* 61:3811-3817 (1993), which is hereby incorporated by reference in its entirety). Glucosyltransferases play an essential role in the etiology and pathogenesis of dental caries by promoting the sucrose dependent adherence of cariogenic streptococci on smooth surfaces and the subsequent development of dental plaque (Smith et al., "Effects of Local Immunization with Glucosyltransferase on Colonization of Hamsters by *Streptococcus Mutans*," *Infect Immun* 37:656-661 (1982); Hamada et al., "Virulence Factors of *Streptococcus Mutans* and Dental Caries Prevention," *J Dent Res* 63:407-411 (1984); Tanzer et al., "Virulence of Mutants Defective in Glucosyltransferase, Dextran-Meditated Aggregation, or Dextranase Activity," p. 204-211. In S. A. Mergenhagen and B. Rosan (ed.), *Molecular Basis of Oral Microbial Adhesion*. American Society for Microbiology, Washington, D.C. (1985); and Tsumori et al., "The role of the *Streptococcus Mutans* Glucosyltransferases in the Sucrose-Dependent Attachment to Smooth Surfaces: Essential Role of the Gtf-C Enzyme," *Oral Microbiol Immunol* 12:274-280 (1997), which are hereby incorporated by reference in their entirety).

The colonization of smooth surfaces by mutans streptococci has been correlated with high caries activities in young children and the synthesis of insoluble glucan has been shown to contribute to caries development in infants and toddlers by increasing the adherence of mutans streptococci and their accumulation in dental plaque (Alaluusua et al., "*Streptococcus Mutans* Establishment and Dental Caries in Children from 2 to 4 years old," *Scan J Dent Res* 91:453-457 (1983); Köhler et al., "The Earlier the Colonization by Mutans Streptococci, the Higher the Caries Prevalence at 4 Years of Age," *Oral Micrbiol Immunol* 3:14-17 (1988); and Mattos-Graner et al., "Water-Insoluble Glucan Synthesis by Mutans Streptococcal Strains Correlates with Caries Incidence in 12- to 30-month-old Children," *J Dent Res* 79:1371-1377 (2000), which are hereby incorporated by reference in their entirety). These investigators showed that the population of mutans streptococci in the saliva of caries-free and caries-active toddlers was quantified, and the bacteria were isolated and analyzed for their ability to produce glucan and adhere to glass surfaces (Mattos-Graner et al., "Water-Insoluble Glucan Synthesis by Mutans Streptococcal Strains Correlates with Caries Incidence in 12- to 30-month-old Children," *J Dent Res* 79:1371-1377 (2000), which is hereby incorporated by reference in its entirety). This group also found positive correlations between mutans streptococci levels in saliva and caries prevalence, between Gtf activities of the mutans streptococci and caries prevalence, and between Gtf activities of the bacteria and the abilities of the bacteria to adhere to glass surfaces (Mattos-Graner et al., "Water-Insoluble Glucan Synthesis by Mutans Streptococcal Strains Correlates with Caries Incidence in 12- to 30-month-old Children," *J Dent Res* 79:1371-1377 (2000), which is hereby incorporated by reference in its entirety). Clearly, the synthesis of glucan contributes to the virulence of mutans streptococci in dental caries (Krasse et al., "The Effects of Caries-Inducing Streptococci in Hamsters Fed Diets with Sucrose or Glucose," *Arch Oral Biol* 10:223-226 (1965); Hamada et al., "Biology, Immunology, and Cariogenicity of *Streptococcus Mutans*," *Microbiol Rev* 44:331-384 (1980); Curtiss et al., "Analysis of *Streptococcus Mutans* Virulence Attributes Using Recombinant DNA and Immunological Techniques," p. 95-104. In R. J. Doyle and J. E. Ciardi (ed.), *Glucosyltransferases, Sucrose, and Dental Caries. Spec. Suppl Chemical Senses*. IRL Press, Washington, D.C. (1983); Hamada et al., "Virulence Factors of *Streptococcus Mutans* and Dental Caries Prevention," *J Dent Res* 63:407-411 (1984); Tanzer et al., "Virulence of Mutants Defective in Glucosyltransferase, Dextran-Meditated Aggregation, or Dextranase Activity," p. 204-211. In S. A. Mergenhagen and B. Rosan (ed.), *Molecular Basis of Oral Microbial Adhesion*. American Society for Microbiology, Washington, D.C. (1985); Koga et al., "Adherence of *Streptococcus Mutans* to Tooth Surfaces," p. 133-143. In S. Hamada, S. Michalek, H. Kiyono, L. Menaker, and J. R. McGhee (ed.), *Molecular Microbiology and Immunology of Streptococcus Mutans*. Elsevier Science Publishers, Amsterdam (1985); Loesche et al., "Role of *Streptococcus Mutans* in Human Dental Decay," *Microbiol Rev* 50:353-380 (1986); Drake et al., "Specificity of the Glucan-Binding Lectin of *Streptococcus Cricetus*," *Infect Immun* 56:1864-1872 (1988); and Kuramitsu et al., "Virulence Factors of Mutans Streptococci: Role of Molecular Genetics," *Crit Rev Oral Biol Med* 4:159-176 (1993), which are hereby incorporated by reference in their entirety) and has been shown to modify the chemical properties of dental plaque and enhance it's cariogenicity (van Houte et al., "Increased pH-Lowering Ability of *Streptococcus Mutans* Cell Masses Associated with Extracellular Glucan-Rich Matrix Material and the Mechanisms Involved," *J Dent Res* 68:451-459 (1989), which is hereby incorporated by reference in its entirety).

The study described in Examples 6 and 7 revealed a strong correlation of the presence of GtfB, as determined by ELISA, using monoclonal antibodies, with the number of clinical lesions of pediatric subjects. A correlation between total Gtf activity and DFS scores was not found. It is possible that a significant amount of activity was measured when the saliva was clarified due to the adsorption of enzymes to surface of bacteria. The ability to measure the level of a proven virulence factor and correlate it with caries activity represents an enormous step forward in diagnosis of caries. It is therefore expected that the anti-GtfB antibodies can be used as a basis for a diagnostic or prognostic assay for ECC.

Data from several tests show a correlation of caries with DMFS or DMFT in large populations, especially adults. For example, some methods determine the salivary and plaque populations of cariogenic microorganisms such as lactobacilli and streptococci (Duchin et al., "Relationship of *Streptococcus Mutans* and Lactobacilli to Incipient Smooth Surface Dental Caries in Man," *Archs Oral Biol* 23:779-786 (1978); Köhler et al., "Practical Method to Facilitate Estimation of Streptococcus Mutans Levels in Saliva," *J Clin Microbiol* 9:584-588 (1979); Beighton et al., "The Value of Salivary Bacterial Counts in the Prediction of Caries Activity," p. 313-326. In N. W. Johnson (ed.), *Risk Markers for Oral Diseases. Dental Caries*. Cambridge, Cambridge University Press (1991); Eisenberg et al., "Associations of Microbiological Factors and Plaque Index with Caries Prevalence and Water Fluoridation Status," *Oral Microbiol* and Immunol 6:139-145 (1991); Leverett et al., "Caries Risk Assessment by a Cross-Sectional Discrimination Model," *J Dent Res* 72: 529-537 (1993); and Leverett et al., "Caries Risk Assessment in a Longitudinal Discrimination Study," *J Dent Res* 72: 529-537 (1993), which are hereby incorporated by reference in their entirety). Other methods have been used to identify aciduric and acidogenic organisms in saliva or in plaque, such as the Swab test and the Snyder test (Snyder et al., "Laboratory Methods in the Clinical Evaluation of Caries Activity," *J Am Dents Ass* 41:400 (1951); and Grainger et al., "Swab Test for Dental Caries Activity: an Epidemiological Study," *J Can Dent Ass* 31:515 (1965), which are hereby incorporated by reference in their entirety). These tests are based on calorimetric measure of pH changes in culture media inoculated with either saliva or plaque samples. The enzyme assays measure activity of all Gtfs of *S. mutans* in saliva, and does not distinguish soluble glucan from insoluble glucan. In contrast, the ELISA measures presence of each enzyme. GtfB synthesizes insoluble glucan binds to bacteria and contributes significantly to the bulk of plaque (Critchley et al., "The Breakdown of the Carbohydrate and Protein Matrix of Dental Plaque," *Caries Res* 3:249-265 (1969); Critchley et al., "The Microbiology of Dental Plaque with Special Reference to Polysaccharide Formation," *Dtsh Zah Zeitschrift* 26:1155-1161 (1971); Critchley et al., "The Polymerisation of Dietary Sugars by Dental Plaque," *Caries Res.* 1:112-129 (1967); Critchley et al., "The Histology and Histochemistry of Dental Plaque," *Caries Res.* 2:115-129 (1968); Loesche et al., "Role of *Streptococcus Mutans* in Human Dental Decay," *Microbiol Rev* 50:353-380 (1986); and Hanada et al., "Isolation and Characterization of the *Streptococus Mutans* gtfD gene, Coding for Synthesis of Primer Dependent Soluble Glucan Synthesis," *Infect Immun.* 57:2079-2085 (1989), which are hereby incorporated by reference in their entirety).

An ideal test for caries activity is one that can predict caries activity prior to the onset of lesions. The best predictor of future caries experience thus far involves assessing the presence of carious lesions already present on tooth surfaces (Grainger et al., "Determination of Relative Caries Experience," *J Can Dent Ass* 26:531 (1960); Stamm et al., "The University of North Carolina Caries Risk Assessment Study: Final Results and Some Alternative Modeling Approaches," p. 209-234, In W. H. Bowen and L. A. Tabak (ed.), *Cariology for the Nineties*. University of Rochester Press, Rochester (1993); Hausen et al., "Caries Prediction-State of the Art," *Community Dent Oral Epidemiol* 25:87-96 (1997); Powell et al., "Caries Prediction: a Review of the Literature," *Community Dent Oral Epidemiol* 26:361-371 (1998); and Messer et al., "Assessing Caries Risk in Children," *Aust Dent J* 45:6-10 (2000), which are hereby incorporated by reference in their entirety). For example, investigators at the University of North Carolina performed a caries risk assessment study involving over 5,000 children, ages 6-11 years old, in low fluoride communities in both South Carolina and Maine. The investigators used several criteria to predict future caries risk including clinical, microbiological, socio-demographic and health behavior variables and found that clinical variables, such as the presence of carious lesions, were the most powerful predictors of future caries risk (Stamm et al., "The University of North Carolina Caries Risk Assessment Study: Final Results and Some Alternative Modeling Approaches," p. 209-234, In W. H. Bowen and L. A. Tabak (ed.), *Cariology for the Nineties*. University of Rochester Press, Rochester (1993), which is hereby incorporated by reference in its entirety).

The data and results described in Examples 6 and 7 represent a radical departure from the status quo, offering a simple and reliable assay to assess caries activity and predict susceptibility to caries. The experimental analyses presented in Examples 6 and 7 are significant and innovative because (a) they are the first to measure directly for the presence/activity, in saliva, of a proven virulence factor of dental caries, (b) the virulence factor appears in saliva, which is easily obtained from a patient, and (c) early childhood caries is a disease that appears in children at a very young age and in a very tight time frame.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of diagnosing predisposition of a human child to early childhood caries, said method comprising:
providing an antibody that specifically binds to a glucosyltransferase B (GtfB) enzyme from a cariogenic *Streptococcus;*
obtaining a saliva sample from a human child prior to onset of carious lesions;
centrifuging the obtained saliva sample to produce a clarified saliva sample;
contacting the antibody with the clarified saliva sample under conditions effective to yield a detectable signal if the GtfB enzyme is present in the clarified saliva sample and if the antibody binds to the GtfB enzyme; and
quantifying the amount of GtfB enzyme in the clarified saliva sample based on the detectable signal, wherein an increase in the amount of GtfB enzyme present in the clarified saliva sample, as compared to an amount of GtfB enzyme present in a clarified saliva sample from a caries-free human child, indicates that the human child is predisposed to early childhood caries.

2. The method according to claim 1, wherein the antibody is selected from the group consisting of a monoclonal antibody, a mono-specific polyclonal antiserum, and combinations thereof.

3. The method according to claim 1, wherein the detectable signal is selected from the group consisting of an immunochemical signal, a fluorescent signal, a radioactive signal, a nuclear magnetic resonance active signal, a luminescent signal, and a chromophore signal.

4. The method according to claim 1, wherein the GtfB enzyme is from *Streptococcus mutans*.

5. The method according to claim 1, wherein the human child is under 8 years of age.

6. The method according to claim 1, wherein the human child is under 6 years of age.

7. The method according to claim 1, wherein the human child is under 4 years of age.

* * * * *